(12) United States Patent
Stanley et al.

(10) Patent No.: US 6,491,717 B1
(45) Date of Patent: Dec. 10, 2002

(54) PULSATING LIQUID SATURATED FOAM CONTAINER

(76) Inventors: Eric D. Stanley, 12550 Wolff St., Denver, CO (US) 80020; Kirk A. Stanley, 12550 Wolff St., Denver, CO (US) 80020

( * ) Notice: Subject to any disclaimer, the term of this patent is extended or adjusted under 35 U.S.C. 154(b) by 202 days.

(21) Appl. No.: 09/635,750

(22) Filed: Aug. 10, 2000

Related U.S. Application Data

(63) Continuation-in-part of application No. 09/414,415, filed on Oct. 7, 1999, now Pat. No. 6,128,795, which is a division of application No. 08/843,744, filed on Apr. 21, 1997, now Pat. No. 5,991,948, which is a continuation-in-part of application No. 08/331,183, filed on Oct. 28, 1994, now Pat. No. 5,632,051.

(51) Int. Cl.[7] .................................................. A61F 7/00
(52) U.S. Cl. .......................... 607/108; 607/96; 607/104
(58) Field of Search ................................ 607/104, 108, 607/109, 110, 111, 96; 5/421, 422, 655.5, 670, 674, 678, 680

(56) References Cited

U.S. PATENT DOCUMENTS

| | | | |
|---|---|---|---|
| 2,548,547 A | | 4/1951 | Melrose |
| 3,585,356 A | | 6/1971 | Hall et al. |
| 3,600,726 A | | 8/1971 | Williams |
| 3,611,455 A | | 10/1971 | Gottfried |
| 3,867,939 A | * | 2/1975 | Moore et al. ............... 604/291 |
| 3,872,526 A | | 3/1975 | Betts |
| 4,114,215 A | | 9/1978 | Santo |
| 4,245,361 A | | 1/1981 | Evanson |
| 4,332,043 A | | 6/1982 | Larson |
| 4,411,033 A | | 10/1983 | Morgan |
| 4,532,662 A | * | 8/1985 | Sama ............................. 5/679 |
| 4,607,405 A | * | 8/1986 | Ellis et al. ...................... 5/670 |
| 4,837,880 A | * | 6/1989 | Coffman ........................ 5/670 |
| 5,016,618 A | | 5/1991 | Simmons |
| 5,175,898 A | | 1/1993 | Johenning et al. |
| 5,222,262 A | | 6/1993 | Boyd |
| 5,435,765 A | * | 7/1995 | Fletcher ......................... 4/583 |
| 5,632,051 A | | 5/1997 | Stanley et al. |
| 5,842,241 A | | 12/1998 | Cooper et al. |
| 5,991,948 A | | 11/1999 | Stanley et al. |
| 6,044,506 A | * | 4/2000 | Valene .......................... 5/653 |

\* cited by examiner

Primary Examiner—Linda C. M. Dvorak
Assistant Examiner—Kenneth Schopfer
(74) Attorney, Agent, or Firm—Lee G. Meyer; Meyer & Associates, P.C.

(57) ABSTRACT

A thermally regulatable, pulsating cushioning device having a deformable outer membrane being adapted to sealably receive a liquid material therein; a foam core being encased within and in intimate contact with, but not bonded to the flexible, deformable outer membrane wherein the foam core has a dimension substantially coincident with the outer membrane; a liquid material, sealably contained within the flexible, deformable outer membrane and saturating the foam core, with the liquid material being at least partially circulatable throughout the foam core, wherein the cooperation of the saturated foam core and the sealable flexible membrane provide a uniform, thermally regulatable medium and structural support such that the pulsating cushioning device is readily, uniformly deformable when a load is applied thereto; a means for directly pulsating the liquid within the flexible, deformable outer membrane, causing the device to undulate or vibrate; and a thermal regulator cooperating with the liquid material to either heat or cool the liquid material.

34 Claims, 1 Drawing Sheet

PULSATING LIQUID SATURATED FOAM CONTAINER

The present application is a Continuation-in-Part of application Ser. No. 09/414,415 filed Oct. 7, 1999 now U.S. Pat. No. 6,128,795 issued Oct. 10, 2000 for a Fluid Saturated Foam Container which is a Divisional of application Ser. No. 08/843,744 filed Apr. 21, 1997 now U.S. Pat. No. 5,991,948 for a Fluid Saturated Foam Container issued on Nov. 30, 1999 which is a continuation-in-part Ser. No. 08/331,183 filed Oct. 28, 1994 of U.S. Pat. No. 5,632,051 issued May 27, 1997 for a Cooling Fluid Container, all of which are incorporated herein by reference in their entirety. The grand parent application discloses a pillow insert comprising a liquid-saturated, foam-filled container which slides between a pillow case and the top of a pillow to provide a constant cool spot for a pillow user or for a pet cooling bed to make animals and family pets more comfortable.

BACKGROUND OF THE INVENTION

1. Field of the Invention

The parent invention relates to a liquid saturated, foam-filled container as a device for providing simultaneous support of an animal or person placed thereon and thermal regulation of the body of that animal or person which can be enhanced by means of a thermal regulating unit; and, more specifically, to a liquid-saturated, foam-filled, cushioning support device for application in, for example, the medical field, as well as for recreational use. Various aspects of the instant application are directed to a thermally regulatable, pulsating, liquid-saturated, foam-filled container as a device for simultaneously providing support of a person placed thereon and for thermal regulation of the body of that person; and, more specifically, various embodiments of the instant invention are directed to pulsating, liquid-saturated, foam-filled, cushioning support devices for application in, for example, the medical field, wherein the device pulsates or vibrates to stimulate proper blood circulation in a bed-ridden person, thereby preventing bed sores and the like.

2. Description of Related Art

It has long been recognized that there are certain advantages to liquid containing devices, such as water beds, which support and/or act as thermal modulators and contain liquids, such as water, in a flexible or malleable container. The inherent drawbacks of such devices are that the liquid within the container moves freely, without restriction and that the liquid is typically required to bear the entire weight of a person or object placed thereon. Thus, such devices heretofore have relied upon increasing the pressure of the liquid within the container when an object is placed thereon in order to provide support. This typically makes the devices bulky and heavy. Further, when such devices are bent, or "wrapped", around an object, they frequently tend to kink or bind as the liquid becomes partially or totally displaced at the bend.

Many water bed devices exist wherein fillers have been placed within the device in order to avoid wave action or other undesired movement of the liquid within the container or device. Such prior art devices, however, tend to kink or bend when a load is applied, such as when such a device is wrapped around a person's arm, leg, etc. Even multi-chambered apparatuses are not satisfactory since complicated valving devices between chambers are typically required to support movement of the liquid through the device. Other devices employ valves, baffles, fillers, and the like to reduce wave motion and liquid displacement inherent in such liquid filled devices. Still other devices employ gels or deformable plastic type fillers. Although such devices purport to reduce the wave motion and liquid displacement through the device, none provides equalized support coupled with the unrestricted mobility of the water through the device.

Containers or continuous covers, such as sealable vinyl bags and the like, have also been filled with foams of various descriptions in order to alleviate some of the problems inherent in the liquid-filled devices. Though these foam-containing devices typically use an air-filled foam structure as a support, they do not provide the heat transferability of a liquid, nor the capacity for inducing circulatable undulations or pulsations directly through the contained liquid, rather than vibrating the entire device.

Specifically, U.S. Pat. No. 3,872,526 issued to Betts for a "Vibratory Water Bed" discloses a water-filled mattress having a plurality of vibratory units coupled in mechanical communication with the sides of the mattress. A vibratory motor causes mechanical perturbations or vibrations to travel to the mattress and therefore to the body of a person resting thereupon. The disclosed invention is for vibrating a non-foam-filled, "full-motion" water bed. The water in the mattress of the disclosed invention is completely unrestricted and is mechanically vibrated by a vibratory motor coupled to the mattress as a unit.

U.S. Pat. No. 4,114,215 issued to Santo for a "Unitary Accessory Control for a Waterbed" discloses a unitary accessory control unit having a variety of mechanisms for controlling the environment of the room in which the waterbed is located. Among the mechanisms disclosed is an oscillatory motor which vibrates a "full-motion", flexible waterbed bladder and thereby imparts motion to the fluid within the bladder. The mechanical perturbations of the oscillatory motor cause the entire waterbed bladder or mattress to vibrate and do not induce undulations or pulsations directly into the contained fluid itself. Further, the disclosed invention vibrates a non-foam filled waterbed mattress which has complete and unrestricted mobility of the fluid throughout the mattress.

Often, when an individual must lie in a bed in substantially the same position for great lengths of time, a standard foam mattress, waterbed, or other type of bed cushion may cause the patient to experience bed sores or other problems associated with pressure point contact and/or impaired blood circulation, unless the patient is rolled-over or otherwise is aided frequently in altering their body position. It would, therefore, be advantageous to have a lightweight device that afforded the structural support of foam, the heat transferability of a liquid, and the capacity to pulsate, vibrate or undulate the device without the inherent problems presented by unrestricted mobility of a liquid.

SUMMARY OF THE INVENTION

It has now been discovered that by saturating a foam-filled, flexible, liquid-impervious container with a liquid, the structural stability as well as the load bearing ability of the device can be enhanced, while still allowing selected mobility of the liquid by external means to provide beneficial vibratory or pulsating movement, while retaining enhanced thermal regulation, flexibility and mobility, not available with prior art devices.

In accordance with various embodiments of the present invention, there is provided a liquid-saturated, foam-filled, flexible container having a flexible, liquid-impervious outer membrane encapsulating a foam filler of the same dimensions, wherein the foam filler is saturated with a liquid such that the liquid has at least partial mobility through the foam filler, and the foam and the liquid cooperate within the confines of the outer membrane to provide the device with both flexibility and structural stability. In the present invention, the liquid-impervious, flexible container may be substantially filled with a porous foam material which is saturated with a liquid. This contained liquid may be caused directly to undulate or vibrate by allowing pulsating liquid exchange between an outside liquid pulsing source and the inside of the container, thereby affecting stimulation of the circulatory system of a person who is lying upon, or is otherwise in close contact with, the flexible, liquid container as well as helping to eliminate pressure points which cause "bed sores."

The instant invention is ideally suited for use with, for example, the infirm, the elderly, hospital patients, or others who are confined to their beds for extended periods of time and who would otherwise suffer from blood sedimentation, sores, atrophy of muscles and the like. The instant invention, may also eliminate the problems commonly associated with standard mattresses or waterbeds, in that the liquid-saturated foam core of the present invention allows the body weight of the individual to be more evenly distributed, thereby preventing exertion of continuous pressure on the body's "pressure points", or points of contact with the bed or liner, which leads to bed sores and other problems caused by poor blood circulation, while damping or restricting the unfettered flow of liquid present in conventional water beds.

Additionally, the instant invention induces and regulates undulations or pulsations which continually move or vibrate the patient in a soothing yet effective, manner, thus improving blood circulation and preventing bed sores and other contact problems associated with constant pressure of the skin against a surface, such as a mattress pad.

In accordance with various embodiments, there is provided an external device for pulsing or moving liquid between the device and the core of the foam filled, flexible container to effect an undulation or vibration. The device may be capable of moving the liquid in a pulsating manner with varied amplitude and frequency. Thus, a vibration or a slow undulation may be introduced to effect different therapies. In one embodiment, the device is cycled through a program of frequencies and amplitudes to provide a gradually changing movement. In accordance with one aspect the surge is initated and then relaxed. In accordance with another aspect the surge is initiated and then reversed.

The instant foam filled, flexible container device inherently cools and/or heats a person's body by allowing convective heat exchange between a person's body and the liquid encapsulated within the container. The heat is passively dissipated to the surrounding environment. In another embodiment, the liquid is heated and/or cooled by means of a thermal regulator or external heating or cooling device which directly heats or cools the liquid external the container. The heating and cooling device and the pulsating and undulating device thus simultaneously operate on the liquid which is exchanged within the container. In an exemplary embodiment the external thermal regulation and the undulation of the liquid are performed by the same device.

Other objects, features, and advantages of the present invention will become more fully apparent from the following detailed description of the preferred embodiments, the appended claims, and references to the accompanying drawings which form a part of the specification, wherein like reference numbers designate corresponding parts in the several views.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation. Indeed, no element described herein is required for the practice of the invention unless specifically described as "essential" or "required."

DETAILED DESCRIPTION OF THE DRAWINGS

Figure 1:
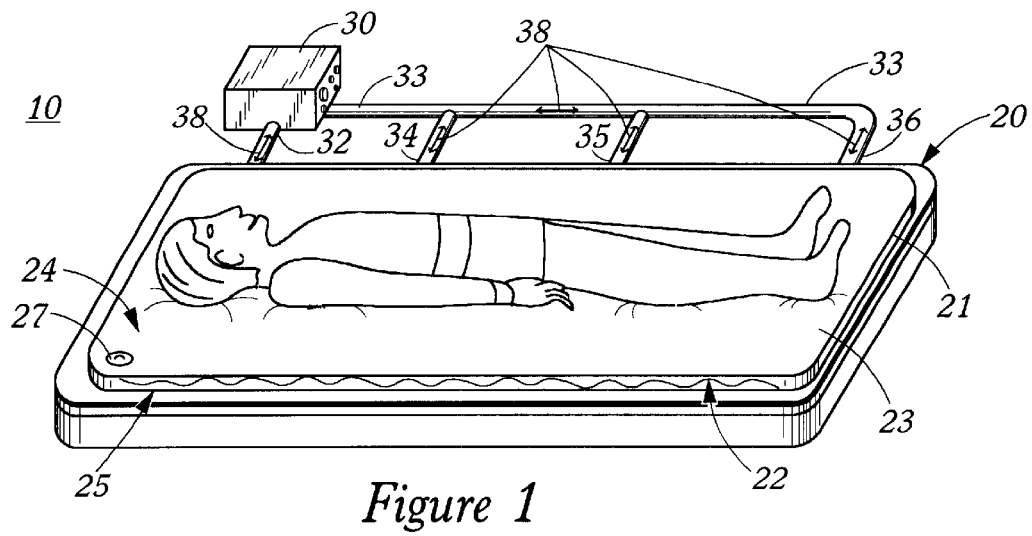
FIG. 1 is a top perspective view of an exemplary embodiment of the pulsating, liquid-saturated, foam container of the present invention having an external pulsating means connected thereto.

Turning to the drawings, there is shown in FIG. 1 a top perspective view of a liquid undulating device 10 of the present invention, wherein a liquid containing bed 20 provides oscillatory or vibratory movement. Device 10 suitably communicates with a pulsator or liquid pulsating unit 30 that, when activated via controls, provides a mechanism for moving water within the bed 20 in an oscillatory or pulsating motion by alternatively increasing and decreasing the pressure through movement of liquid 22. The bed 20 is made to vibrate or undulate by adding or removing liquid 22 from the bed 20 in a controlled manner. The rapidity (frequency), amount (amplitude) and phase of the vibrators may be varied to control the level of oscillatory movement in the bed 20. Manifold 33 and liquid transfer tube 32 are suitably coupled to unit 30 to facilitate flow of liquid 22. Tube 32 and manifold 33, which also communicates with liquid transfer tubes, 34, 35 and 36 situated along the horizontal axis of bed 20, are in communication with the core of the bed 20.

The unit 30 undulates bed 20 by, any suitable technique for example, unit 30 may apply positive surges that are then relaxed. In this method for vibrating the bed 20, liquid 22, is caused to surge in an oscillatory motion into and out of the core of bed 20 by a pulsating surge of liquid from unit 30 which is then relaxed. In the initial surge, unit 30 pushes liquid 22 forward through tube 32 to the bed 20 and through manifold 33, through liquid transfer tubes 34, 35, and 36 into the bed 20 as illustrated by arrows 38. The surge may then be relaxed as appropriate, and liquid 22 suitably surges from bed 20, back into tubes 32, 34, 35 and 36 as illustrated by arrows 38.

Alternatively, unit 30 may apply a positive surge and followed by a negative surge. In the second method for vibrating the bed 20, liquid 22, is caused to surge in an oscillatory motion into and out of the core of bed 20 by a pulsating surge of liquid from unit 30 followed by a negative surge from unit 30. In this second method a first positive surge is applied by unit 30 by pushing liquid 22 forward through tube 32 to the bed 20 and through manifold 33, liquid transfer tubes 34, 35 and 36 into the bed 20 as illustrated by arrows 38. After applying a positive surge, unit 30 applies a negative surge to draw liquid 22 from bed 22 back into tubes 32, 34, 35 and 36 as illustrated by arrows 38. Of course other pumping, undulating or surging schemes may be formulated in accordance with the various embodiments of the invention. Positive and negative surges may be combined with periods of relaxation, for example. Further, other structures for tube 32 and manifold 33 could be formulated. For example, tube 32 could be implemented as a manifold structure with multiple tube interference to bed 20, or the number of tubes 32, 34, 35, and 36 could be varied from two tubes up to dozens or even hundreds of tubes.

Unit 30 can contain a pulsating pump mechanism (not shown). This action by the pulsator unit 30, may be regulated to cause a pulsating, undulating, or vibrating motion throughout the bed 20 which, though not necessarily perceived by the user lying thereon, is transferred to the body of the patient and effectively stimulates that person's blood circulation as well as shifting the pressure points of body contact with the surface of bed 20.

Figure 2:
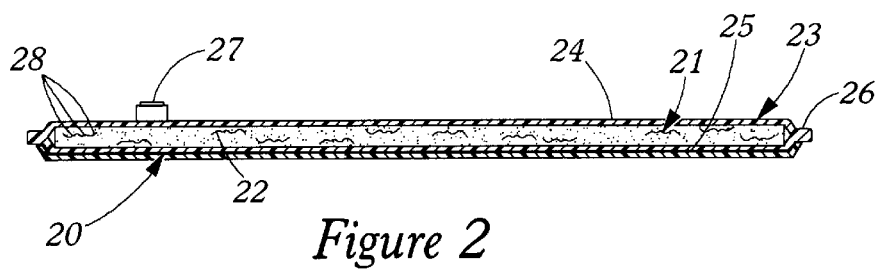
FIG. 2 is a cross-sectional view of the liquid-containing bed of the present invention.

Referring now to FIG. 2, there is shown a sectional view of the construction of the liquid-containing bed 20. A foam core 21, which may become saturated with liquid 22, is snugly enclosed by a vinyl covering or outer membrane 23. The vinyl covering or outer membrane 23 may be composed of an upper vinyl sheet or membrane 24 and a lower vinyl sheet or membrane 25 fused together at 26 by, for example, heat or radio frequency (RF) radiation to form a strong liquid tight seal. The flexible vinyl sheets 24 and 25 are available in thicknesses that range from 2 millimeters to 200 millimeters, and the lower vinyl sheet 25 may, for example, include a non-sliding surface such as, for instance, rubber-studded cloth or vinyl-studded cloth. Bed 20 suitably includes a simple liquid inlet and outlet 27 for introduction and removal of liquid into and out of the bed 20. The liquid inlet and outlet 27 may be attached in a water tight fashion to the vinyl covering 23, and the foam core 21 is saturated with liquid 22. Although the exemplary bed 20 of FIG. 2 has a single inlet 27, it will be appreciated that other embodiments may include multiple inlets.

In accordance with various embodiments, the foam core 21 consists of foam composed of, for example, reticulated polyurethane which contains cell pores 28. The foam core 21 is suitable of an open pore structure to allow substantially free mobility of the liquid within the foam core 21. The foam core 21 is saturated with a liquid 22 such as water or any other liquid. The foam core 21 can be processed with an acid treatment or sonic treatment to result in larger pore sizes and is available in, for example, pore densities ranging from ten pores per inch (PPI) to sixty PPI. A pore density of at least 20 PPI reduces both noise and the risk of leakage if the bed's vinyl covering 23 is punctured or torn. Noise is reduced because liquid 22 is retained in the foam core 21 and not free to audibly "slosh" or "splash" inside of covering 23. Risk of leakage is also reduced because liquid 22 is retained in the foam core 21 and is therefore not as free to leak out of a puncture, cut, or tear. Thus, the foam core 21 tends not to release the liquid 22 or result in leakage unless pressure is applied at or near a puncture or cut. Additionally, because all the liquid 22 may be evenly distributed throughout the core 21 by conduction, for example, the liquid 22 does not tend to pool in one spot. This allows the foam core 21 to act as a weight sink to stabilize the device 10 and prevent the device 10 from slipping out of place.

It will be appreciated that by increasing the closure of the cellular structure of the foam core 21, increased mechanical support is provided by device 10. Increasing the closure of the more closed the cell pores 28, however, may result in less mobility of the liquid 22 within the foam core 21. Hence, less mixing of the liquid 22 contained within the foam core 21 and the greater the pressure required to undulate the liquid may result. It will also be realized that, to be most effective, the liquid 22 should permeate widely to as many of the cell pores 28 as possible. It will further be realized that the liquid 22 can be selected such that certain heat capacity characteristics are imbued to the device as a whole.

Various embodiments of Applicants' present invention utilize the relationship between the sealed vinyl covering 23 and the saturated foam core 21 to provide the medium for the circulation of a pulsating, thermally regulatable liquid material 22 throughout the foam core 21. The foam core 21 of the instant device 10 allows circulability of the liquid 22 within the confines of the bed 20, as there are suitably no complex valving devices disposed in a membrane to move liquid back and forth between sealed compartments. This circulability of the liquid material 22 throughout the foam core 21 further allows the device 10 of the present invention to pulsate or undulate the liquid 22 directly, rather than the bed 20 itself, to effectively, yet gently, enhance the blood circulation of a person lying upon, or otherwise in close contact with, the surface of the bed 20.

Figure 3:
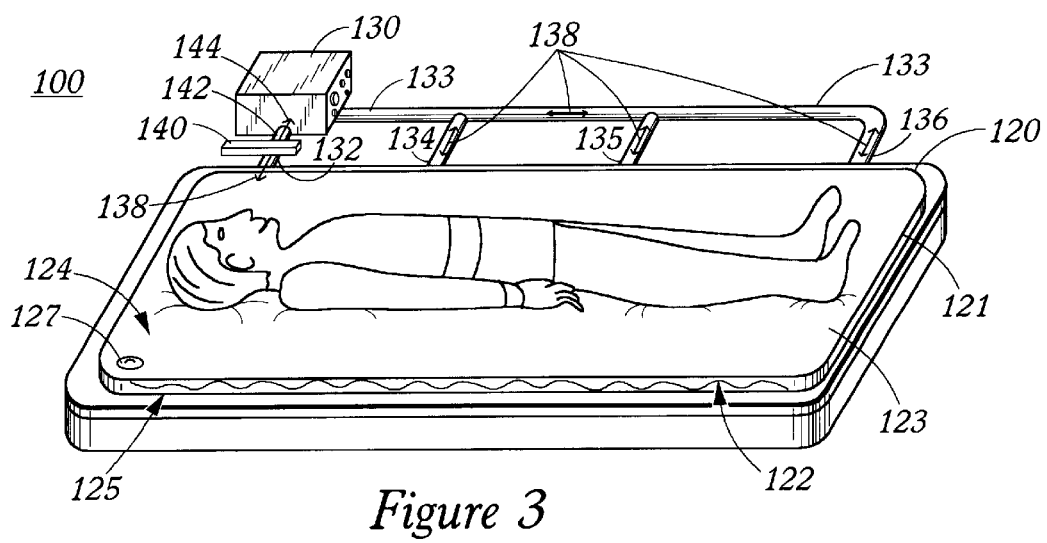
FIG. 3 is a top perspective view of a further embodiment of the pulsating, liquid-saturated, foam container of the present invention having an external liquid thermal regulator and pulsating means connected thereto.

Referring to FIG. 3, there is shown another exemplary embodiment of the liquid undulating device 100. The liquid containing bed 120 provides oscillatory or vibratory movement by means of an external liquid pulsating unit 130 in communication with the liquid containing bed 120. The bed 120 is made to vibrate or undulate by adding or removing liquid 122 from the bed 120 in a controlled manner. Both the rapidity (frequency) and the amount (amplitude) can be varied to control the level of oscillatory movement in the bed 120. Further, the phasing of pulses applied to tube 138 and manifold 133 may be varied. Device 100 contains, a pulsator or liquid pulsating unit 130, that moves water within the bed 120 in an oscillatory or pulsating motion by alternatively increasing and decreasing the pressure through movement of liquid 122. Manifold 133 and liquid transfer tube 132 are responsive to pulses produced at unit 130. Tube 132 and manifold 133, which also communicates with liquid transfer tubes, 134, 135 and 136 situated along the horizontal axis of bed 20, are in communication with the core of the bed 120. Pulsing may be controlled by user input controls (not shown) in communication with unit 130.

Unit 130 may vibrate the bed 120 by, for example, applying a positive surge that then relaxed or by applying intermixed positive and negative surges. In the first method for vibrating the bed 120, liquid 122, is caused to surge in an oscillatory motion into and out of the core of bed 120 by a pulsating surge of liquid from unit 130 which is then relaxed. In the initial surge, unit 130 pushes liquid 122 forward through tube 132 to the bed 120 and through manifold 133, through liquid transfer tubes 134, 135, and 136 into the bed 120 as illustrated by arrows 138. The surge may then be relaxed as liquid 122 surges from bed 120, back into tubes 132, 134, 135 and 136 as illustrated by arrows 138.

In the second method for vibrating the bed 120, liquid 122, may be caused to surge in an oscillatory motion into and out of the core of bed 120 by a pulsating surge of liquid from unit 130 followed by a negative surge from unit 130. In this second method a first positive surge is applied by unit 130 by pushing liquid 122 forward through tube 132 to the bed 120 and through manifold 133, liquid transfer tubes 134, 135 and 136 into the bed 120 as illustrated by arrows 138. Immediately, unit 130 applies a negative surge and the liquid 122 is drawn from bed 122 back into tubes 132, 134, 135 and 136 as illustrated by arrows 138.

As with the embodiment described above in connection with FIG. 2, liquid-containing bed 120 may consist of a foam core 121 saturated with liquid and snugly enclosed by a vinyl covering or outer membrane 123. The vinyl covering or outer membrane 123 may be composed of an upper vinyl sheet or membrane 124 and a lower vinyl sheet or membrane 125 fused together by, for example, heat, RF, or other radiation to form a strong water-tight seal. The lower vinyl sheet 125 may, for example, comprise a non-sliding surface such as, rubber-studded cloth or vinyl-studded cloth. The bed 120 has a simple liquid inlet and outlet 127 for introduction and removal of liquid into and out of the bed 120. The liquid inlet and outlet 127 is attached in a water tight fashion to the vinyl covering 123, and the foam core 121 may saturated with water or another liquid.

The bed 120 of the instant invention suitably communicates with a thermal regulator 140, which when activated via controls thereon, provides an undulation as described above as well as a method of cooling or heating the liquid within the bed 120. To accomplish cooling or heating of the liquid, a liquid transfer tube 132 connects the bed 120 to the regulator 140. A pump mechanism (not shown) causes liquid within the bed 120 to enter liquid transfer tube 132 and be directed toward the regulator 140, as illustrated by arrow 138. The regulator 140 suitably cools or heats the liquid 122 as appropriate, and directs the liquid 122 to the pulsator 130, through liquid transfer tube 142, as illustrated by arrow 144, for surging and directing the liquid back into the bed 120 through the liquid transfer tubes 134, 135 and 136.

Although the present invention has been described with reference to preferred embodiments, numerous modifications and variations can be made and still the result will come within the scope of the invention. No limitation with respect to the specific embodiments disclosed herein is intended or should be inferred.

What is claimed is:

1. A thermally regulatable, pulsating cushioning device comprising:
   (a) a flexible, deformable outer membrane being adapted to sealably receive a liquid material therein;
   (b) a foam core being encased within and in intimate contact with, but not bonded to said flexible, deformable outer membrane wherein said foam core has a dimension substantially coincident with said outer membrane;
   (c) a liquid material being sealably contained within said flexible, deformable outer membrane and saturating said foam core, said liquid material being at least partially circulatable through said foam core wherein the cooperation of said saturated foam core and said sealable flexible membrane provide a substantially uniform, thermally regulatable medium and structural support such that said cushioning device is readily, uniformly deformable when a load is applied thereto; and
   (d) external pulsating means, cooperating with said liquid material, for pulsing said material within said cushioning device.

2. The thermally regulatable, pulsating cushioning device of claim 1 wherein said foam core further comprises reticulated polyurethane foam having a porosity ranging from 10 pores per inch to 60 pores per inch.

3. The thermally regulatable, pulsating cushioning device of claim 1 wherein the outer membrane of said fluid container further comprises vinyl having a thickness ranging from one millimeter to two hundred millimeters.

4. The thermally regulatable, pulsating cushioning device of claim 1 further comprising a resealable inlet and outlet valve for ingress and egress of said liquid material.

5. The thermally regulatable, pulsating cushioning device of claim 1 wherein said flexible outer deformable membrane further comprises a lower outer membrane having a non-sliding surface functioning to hold said device in a predetermined position.

6. The thermally regulatable, pulsating cushioning device of claim 5 wherein said non-sliding surface is a studded cloth chosen from a group consisting of rubber studded cloth and vinyl studded cloth.

7. The thermally regulatable, pulsating cushioning device of claim 1 further comprising a thermal regulator cooperating with the liquid material to either heat or cool the liquid material.

8. The thermally regulatable, pulsating cushioning device of claim 1 further comprising a receiving area adapted to receive a person's body therein, said receiving area having a dimension greater than said body such that said saturated foam core and said outer membrane substantially surround said body.

9. A thermally regulatable, pulsating cushioning device comprising: a plurality of segments of consistent size, each of said segments connectable to at least. one other segment, whereby the length of said device is selectively variable, each of said segments comprising:
   (a) a flexible, deformable outer membrane being adapted to sealably receive a liquid material therein;
   (b) a foam core being encased within and in intimate contact with, but not bonded to, said flexible, deformable outer membrane wherein said foam core has a dimension substantially coincident with said outer membrane;
   (c) a liquid material being sealably contained within said flexible, deformable outer membrane and saturating said foam core, said liquid material being at least partially circulatable through said foam core wherein the cooperation of said saturated foam core and said sealable flexible membrane provides a substantially uniform, thermally regulatable medium and structural support such that said cushioning device is readily, uniformly deformable when a load is applied thereto; and
   (d) external pulsating means, cooperating with said liquid material, for pulsing said liquid material within said cushioning, device.

10. The thermally regulatable, pulsating cushioning device of claim 9, wherein said foam core further comprises reticulated polyurethane foam having a porosity ranging from 10 pores per inch to 60 pores per inch.

11. The thermally regulatable, pulsating cushioning device of claim 9 wherein the outer membrane of said fluid container further comprises vinyl having a thickness ranging from one millimeter to two hundred millimeters.

12. The thermally regulatable, pulsating cushioning device of claim 9 further comprising a resealable inlet and outlet valve for ingress and egress of said liquid material.

13. The thermally regulatable, pulsating cushioning device of claim 9 wherein said flexible outer deformable membrane further comprises a lower outer membrane having a non-sliding surface functioning to hold said device in a predetermined position.

14. The thermally regulatable, pulsating cushioning device of claim 13 wherein said non-sliding surface is a studded cloth chosen from a group consisting of rubber studded cloth and vinyl studded cloth.

15. The thermally regulatable, pulsating cushioning device of claim 9, further comprising a thermal regulator cooperating with the liquid material to either heat or cool the liquid material.

16. The thermally regulatable, pulsating cushioning device of claim 9 further comprising a receiving area adapted to receive a person's body therein, said receiving area having a dimension greater than said body such that said saturated foam core and said outer membrane substantially surround said body.

17. A thermally regulatable, pulsating cushioning device comprising:
(a) a flexible, deformable outer membrane being adapted to sealably receive a liquid material therein;
(b) a foam core being encased within and in intimate contact with, but not bonded to said flexible, deformable outer membrane wherein said foam core has a dimension substantially coincident with said outer membrane,
(c) a liquid material being sealably contained within said flexible, deformable outer membrane and saturating said foam core, said liquid material being at least partially circulatable through said foam core wherein the cooperation of said saturated foam core and said sealable flexible membrane provide a substantially uniform, thermally regulatable medium and structural support such that said cushioning device is readily, uniformly deformable when a load is applied thereto;
(d) external pulsating means, cooperating with said liquid material, for pulsing said liquid material within said cushioning device; and,
(e) a thermal regulator cooperating with the liquid material to either heat or cool liquid material.

18. The thermally regulatable, pulsating cushioning device of claim 17 wherein said foam core further comprises reticulated polyurethane foam having a porosity ranging from 10 pores per inch to 60 pores per inch.

19. The thermally regulatable, pulsating cushioning device of claim 17 wherein the outer membrane of said fluid container further comprises vinyl having a thickness ranging from one millimeter to two hundred millimeters.

20. The thermally regulatable, pulsating cushioning device of claim 17 further comprising a resealable inlet and outlet valve for ingress and egress of said liquid material.

21. The thermally regulatable, pulsating cushioning device of claim 17 wherein said flexible outer deformable membrane further comprises a lower outer membrane having a non-sliding surface functioning to hold said device in a predetermined position.

22. The thermally regulatable, pulsating cushioning device of claim 21 wherein said non-sliding surface is a studded cloth chosen from a group consisting of rubber studded cloth and vinyl studded cloth.

23. The thermally regulatable, pulsating cushioning device of claim 21 further comprising a receiving area adapted to receive a person's body therein, said receiving area having a dimension greater than said body such that said saturated foam core and said outer membrane substantially surround said body.

24. A method for providing a pulsating cushioning device which is readily, uniformly deformable when a load is applied thereto, said device comprising a foam core saturated with a liquid material, said foam core covered by a sealable flexible outer membrane, and said liquid material at least partially circulatable through said foam core and in communication with an external pulsator comprising the step of;
activating said pulsator to pulse said liquid material through said foam core wherein the cooperation of said pulsing liquid material within said saturated foam core and said sealable flexible outer membrane provides a substantially uniform, pulsating medium for structural support.

25. The method of claim 24 wherein said foam core further comprises reticulated polyurethane foam having a porosity ranging from 10 pores per inch to 60 pores per inch.

26. The method of claim 24 wherein said outer membrane of said fluid container further comprises vinyl having a thickness ranging from one millimeter to two hundred millimeters.

27. The method of claim 24 wherein said device comprises a resealable inlet and and outlet valve for ingress and egress of said liquid material.

28. The method of claim 24 wherein said flexible outer membrane further comprises a lower outer membrane having a non-sliding surface functioning to hold said device in a predetermined position.

29. The method of claim 28 wherein said non-sliding surface is a studded cloth chosen from a group consisting of rubber studded cloth and vinyl studded cloth.

30. The method of claim 24 further comprising the steps of:
(a) cooling or heating said liquid material contained within said pulsating, cushioning device by means of a thermal regulator cooperating with said liquid material; and
(b) selectively regulating the temperature of the liquid material with said thermal regulator.

31. The method of claim 24 wherein said device further comprises a receiving area adapted to receive a person's body therein, said receiving area having a dimension greater than said body such that said saturated foam core and said outer membrane substantially surround said body.

32. The method of claim 24 wherein said external pulsator has at least one conduit in communication with said foam core.

33. The method of claim 24 wherein said external pulsator undulates or vibrates said liquid material by surging said liquid through at least one conduit into said foam core and then relaxing.

34. The method of claim 24 wherein said external pulsator undulates or vibrates said liquid material by surging said liquid through at least one conduit and into said foam core and then applying a negative surge.

* * * * *